(12) United States Patent
Doubler et al.

(10) Patent No.: US 7,662,174 B2
(45) Date of Patent: Feb. 16, 2010

(54) SPINAL PLATE WITH SCREW LOCKS AND CAM LOCKS

(75) Inventors: Robert L. Doubler, Ida, MI (US); John E. Hammill, Rossford, OH (US)

(73) Assignee: Spinal, LLC, Palm Beach Gardens, FL (US)

( * ) Notice: Subject to any disclaimer, the term of this patent is extended or adjusted under 35 U.S.C. 154(b) by 187 days.

(21) Appl. No.: 11/344,581

(22) Filed: Jan. 31, 2006

(65) Prior Publication Data

US 2006/0200146 A1 Sep. 7, 2006

Related U.S. Application Data

(63) Continuation-in-part of application No. 11/031,143, filed on Jan. 6, 2005, now Pat. No. 7,322,984.

(51) Int. Cl.
*A61B 17/80* (2006.01)
(52) U.S. Cl. .................................. 606/289; 606/71
(58) Field of Classification Search ............. 606/69–71, 606/280, 286, 289, 293, 295
See application file for complete search history.

(56) References Cited

U.S. PATENT DOCUMENTS

| | | | | |
|---|---|---|---|---|
| 5,549,612 A * | 8/1996 | Yapp et al. | ..................... | 606/69 |
| 6,139,550 A * | 10/2000 | Michelson | .................... | 606/69 |
| 6,306,139 B1 * | 10/2001 | Fuentes | ........................ | 606/70 |
| 6,361,537 B1 * | 3/2002 | Anderson | ................. | 606/86 B |
| 6,413,259 B1 * | 7/2002 | Lyons et al. | .................. | 606/69 |
| 6,503,250 B2 * | 1/2003 | Paul | ........................... | 606/279 |
| 6,602,255 B1 * | 8/2003 | Campbell et al. | ............. | 606/69 |
| 6,652,525 B1 * | 11/2003 | Assaker et al. | ................ | 606/61 |
| 6,755,833 B1 * | 6/2004 | Paul et al. | ..................... | 606/70 |
| 6,893,444 B2 | 5/2005 | Orbay | | |
| 7,452,370 B2 * | 11/2008 | Anderson | ................... | 606/296 |
| 2005/0187551 A1 | 8/2005 | Orbay et al. | | |

* cited by examiner

*Primary Examiner*—Eduardo C Robert
*Assistant Examiner*—Ellen C Hammond
(74) *Attorney, Agent, or Firm*—McHale & Slavin, P.A.

(57) ABSTRACT

A bone plate for stabilizing adjacent vertebrae or ends of a bone having a span for extending across the discontinuity. The span has brackets for attaching to the bone. The brackets have countersunk apertures terminating through which bone screws are placed in the bone. An cam bore is located between the countersunk apertures and a cam with lobe surfaces is positioned in the cam bore. Upon rotation of the cam, the lobe surfaces engage an end of the wedge shoes and move them so that the other end of the wedge shoes move into the countersunk apertures and frictionally engage the heads of the bone screws. The wedge shoe is provided with means to lock the cam in position. The wedge shoe is also provided with means to indicate that the shoe has completely engaged the head of the bone screw in the countersunk aperture.

18 Claims, 4 Drawing Sheets

US 7,662,174 B2

SPINAL PLATE WITH SCREW LOCKS AND CAM LOCKS

RELATED APPLICATIONS

This application is a continuation in part of U.S. patent application Ser. No. 11/031,143 filed Jan. 6, 2005, now U.S. Pat. No. 7,322,984 and is related to U.S. patent application Ser. No. 11/124,455, filed May 6, 2005, which is incorporated herein by reference.

FIELD OF THE INVENTION

This invention relates to the field of orthopedic surgery and to bone plates which are affixed to bone by screws or other fastening devices including spinal plates for the cervical, thoracic and lumbar regions.

BACKGROUND OF THE INVENTION

The use of bone pins and plates for reducing fractures is well known in orthopedic medicine. The pins and plates extend across discontinuities in a bone to fix the broken ends in relation to each other to reduce pain and promote rapid healing without deformity. These devices are secured to the bone by bone screws or nails driven into the bone. More recently, pins, rods, plates and cages have been used to stabilize bone and joints that have deteriorated naturally or as a result of prior trauma.

The interface between the bone screws and the bone presents problems of stability and long term usage that have been addressed in different ways. One of the major problems is usually termed as back-out. This defines the condition in which the fastening devices attaching the plate to the bone loosen over time, either relative to the bone or the plate or both. Severe back-out results in the bone screw working itself out of the bone and/or plate resulting in instability of the bone or joint. This situation results in increasing pain and danger from the instability, as well as, the movement of the screw. There may be several reasons for the back-out but anatomical stresses from body movements contributes greatly to the problem.

Spinal bone plates are usually attached to adjacent vertebrae to reduce pain due to injury or deterioration of the intermediate disk. The plate spans the intervertebral space to stabilize the vertebrae. Pedicle screws or bone screws are inserted through apertures in the opposite ends of the plate into the respective vertebrae or on opposite sides of a break. Due to anatomical forces on the skeleton, the screws sometimes back out of the bones and plates.

What is needed in the art is a bone plate with an internal screw lock that rotates to wedge the bone screws to the plate. Also, an arrangement of the bone screws to permit the use of a narrow bone plate.

DESCRIPTION OF THE PRIOR ART

Prior art devices address the problem of back-out by use of secondary locking screws that hold the bone screws in the plate. The locking device engages the head of the bone screw and is tightened to fix the screw to the plate and, thus, the bone. Such devices are not particularly suited for deployment on the anterior aspect of the spine because of the close proximity of vital soft tissue organs which dictate a smooth, low profile, contoured surface. Michelson, U.S. Pat. No. 6,454,771, discloses a bone plate for anterior cervical fixation. The plate has several holes for receiving bone screws. A locking screw mechanism is used to overlay the screw heads.

An expandable insert for placement between vertebrae is disclosed by Paes et al, U.S. Pat. No. 6,436,142. The device is in the nature of a lag screw and can expand with the insertion of an expansion screw.

U.S. Pat. No. 6,342,055 to Eisermann et al discloses a bone plate with bone screws having a snap-in retainer securing the heads to the plate.

Geisler, U.S. Pat. No. 6,231,610, discloses a bone plate with diverging bone screws and serrations on the plate to increase holding power.

U.S. Pat. No. 6,224,602 to Hayes discloses a bone plate with multiple bone screw holes which may be covered by a sliding locking plate. The bone plate has an undercut channel to hold the locking plate in contact with the screw heads. The locking plate is held to the plate by a locking screw once it is slid to the desired position.

Aust et al, U.S. Pat. No. 5,603,713, discloses an anterior lumbar plate attached by screws with various angular connections to the spine.

Published application, US 2004/0102773 A1, to Morrison et al, uses the ends of the bone plate to cover the heads of the bone screws.

U.S. Pat. No. 6,740,088 B1, to Kozak et al uses extra set screws to interfere with the heads of the bone screws.

U.S. Pat. No. 6,730,127 B2 to Michelson attaches an overlay to the plate to partially cover the heads of the screws.

What is needed in the art is a bone plate with an internal screw lock that rotates to wedge the bone screws to the plate. Also, an arrangement of the bone screws and screw lock to permit the use of a narrow bone plate.

SUMMARY OF THE INVENTION

Disclosed is a bone plate for stabilizing adjacent vertebrae. The plate is formed from a span of rigid material for bridging intervertebral space, the span of material having a bone engaging surface and a distal surface. A first bracket is located at one end of the span and a second bracket is located at the other end of the span. The first bracket includes a first bone fastener aperture and a second bone fastener aperture therethrough with a cam bore between the first bone fastener aperture and the second bone fastener aperture. A first slot in the first bracket extends from the first bone fastener aperture to the cam bore. A second slot in the first bracket extends from the second bone fastener to the cam bore. An eccentric cam is mounted in the cam bore, the cam includes cam surfaces. The first and second bone fastener apertures and the cam bore are not in line with each other. The first and second bone fastener apertures are offset from the cam bore at an approximately 45° angle thereby forming a "V". This arrangement permits the bone fasteners to be located closer to each other so that the width of the bone plate can be decreased.

A first wedge shoe is slidably disposed in the slot between the cam and the first bone fastener aperture for contacting the cam surface. A second wedge shoe is slidably disposed in the slot between the cam and the second bone fastener aperture for contacting the cam surface. Rotating the cam slides the first and second wedge shoes partially into the first and second bone fastener apertures. A cam cover plate can be used to close the slots.

Accordingly, it is a objective of the instant invention to provide a bone plate with an arrangement of bone fasteners which permit the use of an narrower than normal bone plate.

It is a further objective of the instant invention to provide a bone plate with an integral screw lock.

It is yet another objective of the instant invention to provide a bone plate with sliding wedge shoes for locking the bone screws.

It is a still further objective of the instant invention to provide a low profile bone plate with countersunk bone screw apertures therethrough which also have wedge shoe openings.

It is still yet another objective of the instant invention to provide a bone plate to span a plurality of discontinuities in the bone.

Other objects and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

DETAILED DESCRIPTION OF THE INVENTION

While the present invention is susceptible of embodiment in various forms, there is shown in the accompanying drawings and will hereinafter be described a presently preferred embodiment with the understanding that the present disclosure is to be considered an exemplification of the invention and is not intended to limit the invention to the specific embodiments illustrated.

Figure 1:
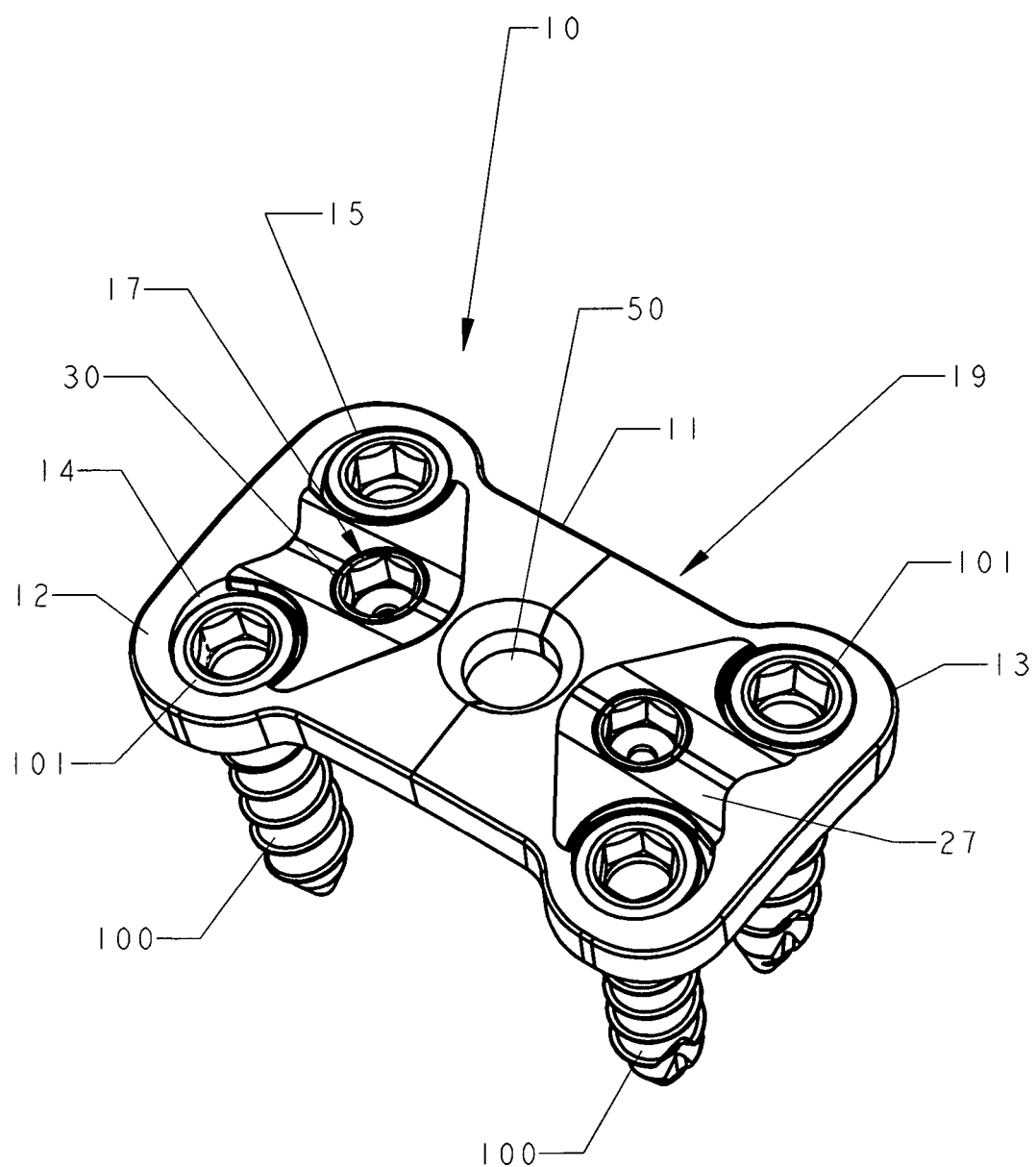
FIG. 1 is a perspective view of the distal side of the assembled bone plate and threaded screw fasteners of the instant invention.
Figure 2:
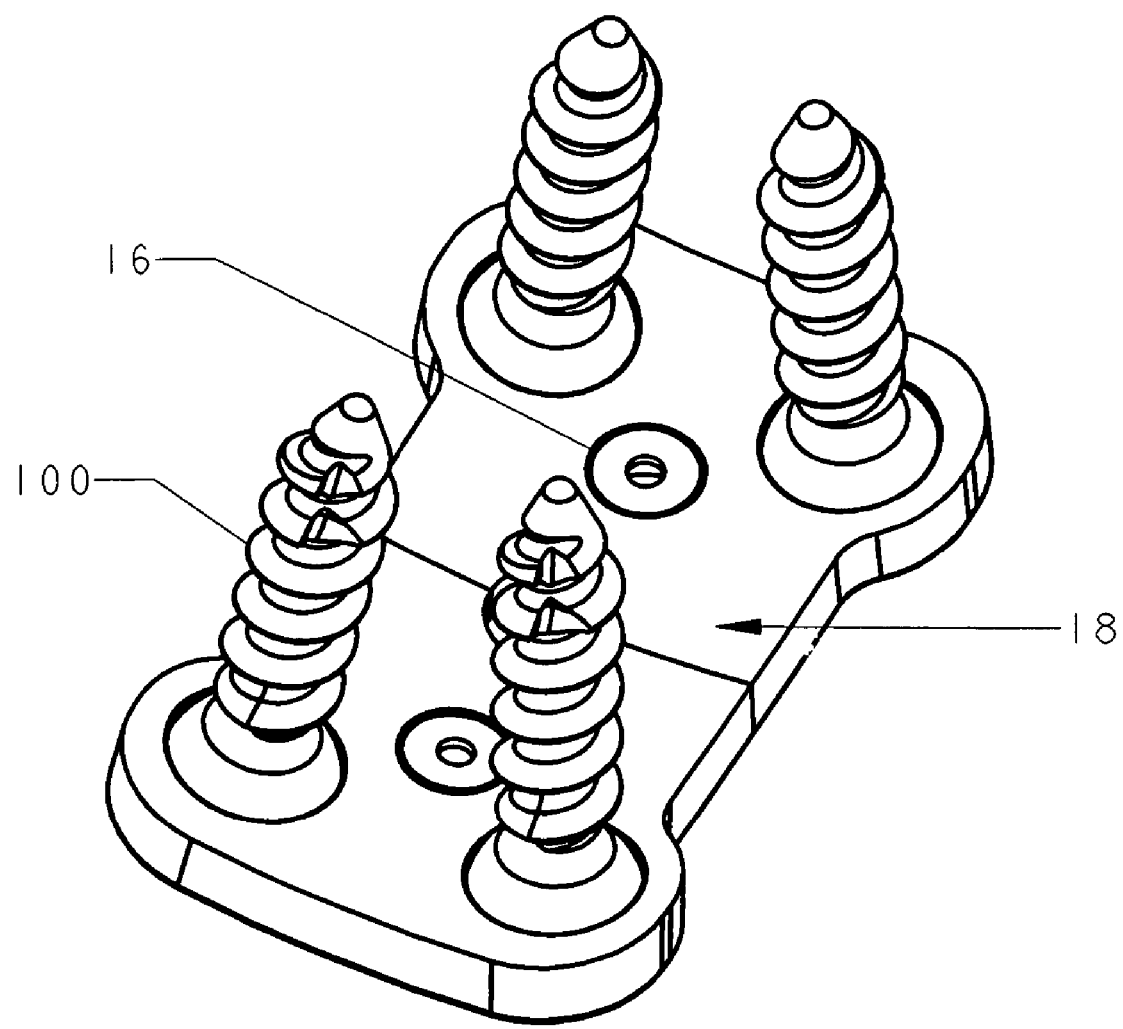
FIG. 2 is a perspective view of the bone engaging side of the assembled bone plate and threaded screw fasteners of the instant invention.
Figure 4:
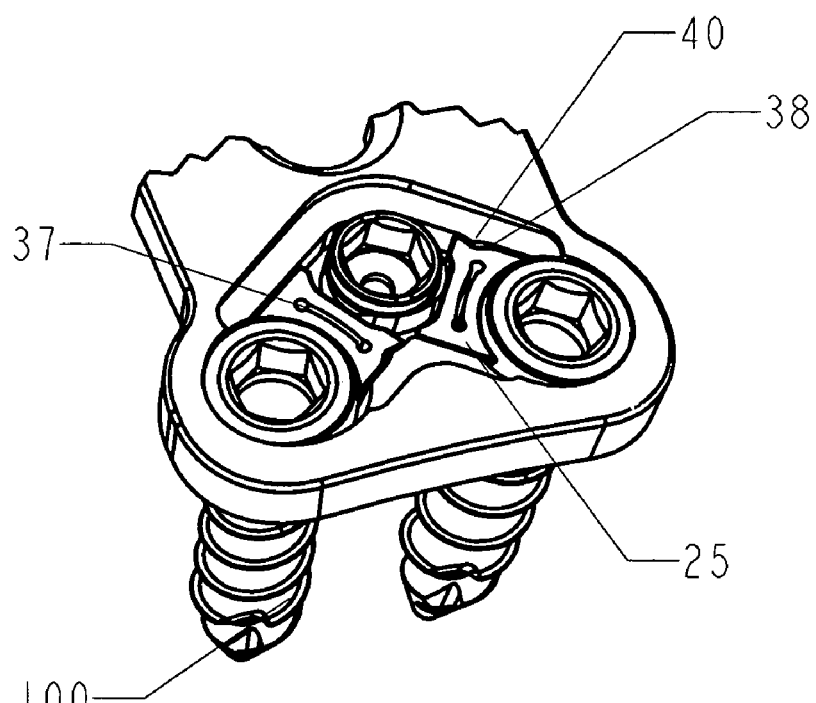
FIG. 4 is a partial perspective view of the bone plate of the instant invention with the cam cover removed.
Figure 5:
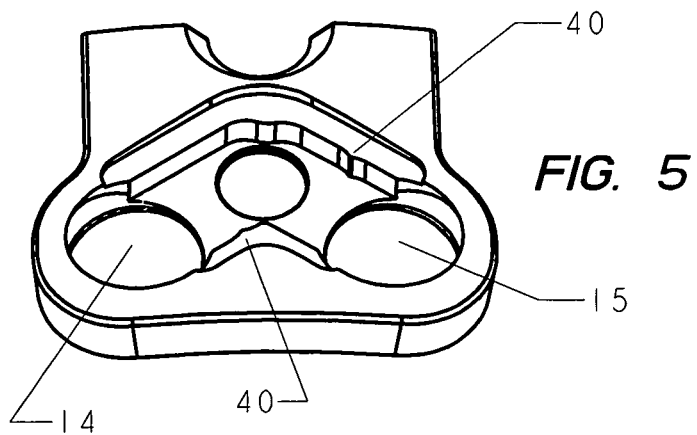
FIG. 5 is a partial perspective view of the wedge shoe recess.

The bone plate 10, shown in FIGS. 1, 2, and 4 is based on an elongated span 11 having a first end and a second end with a first bracket 12 on the first end constructed and arranged to engage a first vertebrae (not shown) and a second bracket 13 on the second end constructed and arranged to engage a second vertebrae (not shown). The bone plate also has two major surfaces, a bone engaging surface 18 and a distal surface 19. A first bracket 12 includes a first bone screw aperture 14 and a second bone screw aperture 15. A cam 17 is located therebetween and offset toward the center portion of the bone plate. This offset enables the bone screw apertures 14 and 15 to be located closer to each other than if the cam 17 were positioned in between the apertures and in line with the apertures. This in turn permits the width of the bone plate 10 to be decreased.

Figure 7:
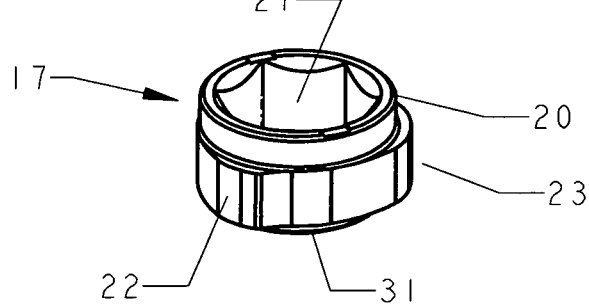
FIG. 7 is a perspective view of the eccentric cam.

The composition of the bone of the vertebrae, the size of the vertebrae and other factors usually determine the size of the bone screw that will be employed to install the bone plate. Should a bone plate with a narrow width be required for a specific condition, the offset of the cam with respect to the bone screws will permit the use of a narrow bone plate. Each of the bone screw apertures 14 and 15 are provided with a countersunk portion or bore so that the head 101 of the bone screw 100 will be approximately level with the distal surface 19 of the bone plate 10. Bone or Pedicle screws 100 are shown in the apertures with the screw heads 101 resting in the countersunk portions or bores of the apertures 14 and 15. This construction contributes to the low profile of the installed bone plate thereby preventing undue trauma to the tissue on the anterior aspect of the cervical spine. Pins 200, shown in FIG. 4, may be used in place of the bone screws. In addition, other known bone fasteners may also be employed. The size of the pedicle screw or other fastener will normally be a determining factor in the overall width of the bone plate 10. A rotating eccentric cam 17, shown in FIG. 7 is mounted in the cam bore 16, as shown in FIG. 2. Its operation will be described later.

The second bracket 13 has the same components as the first bracket 12. An aperture 50 is located in the span 11 which connects the first and second brackets. The aperture 50 serves to promote boney ingrowth which leads to increased stability of the bone plate. As an alternate embodiment, the bone plate may be formed with a series of brackets spaced apart by multiple spans for use when several vertebrae are to be stabilized.

The bone screw apertures 14 and 15 extend through the bone plate from the bone engaging surface to the distal surface. The cam bore 16 in the bone engaging surface is circular and serves as a guide and bearing surface for the end 31 of the actuator 20 of the eccentric cam 17. The cam actuator 20 has a receptacle 21 located in a central axial portion thereof. A tool, such as an allen wrench (not shown), cooperates with the receptacle 21 to rotate the cam 17. The top surface of the distal end of the cam 17 is approximately level with the distal surface of the bone plate. The cam 17 is also provided with eccentric cam lobe surfaces 22 and 23. The cam lobe surfaces are formed approximately 45° apart in a preferred embodiment.

Figure 3:
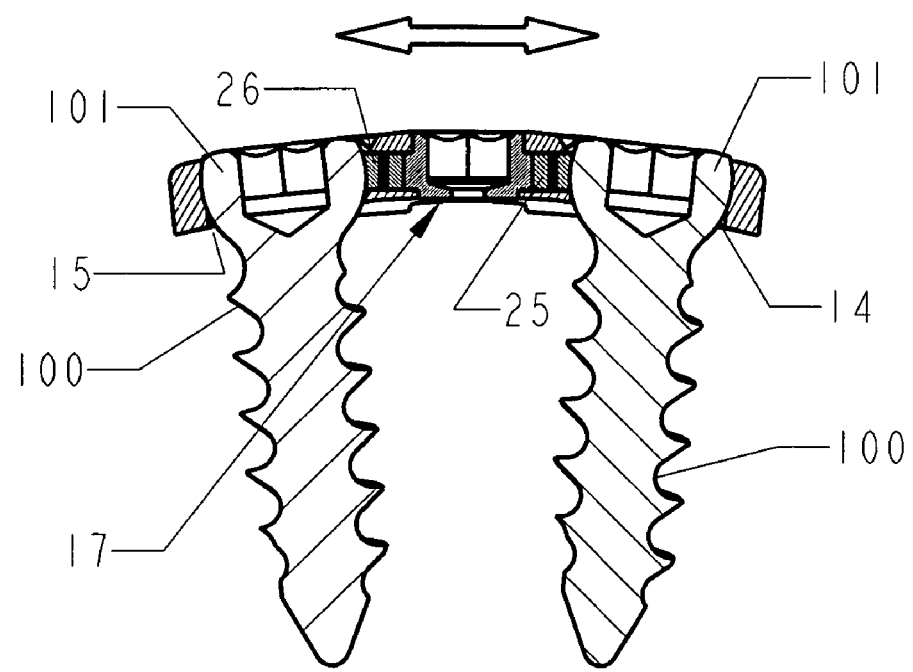
FIG. 3 is a transverse cross section of a bone plate of the instant invention.
Figure 8:
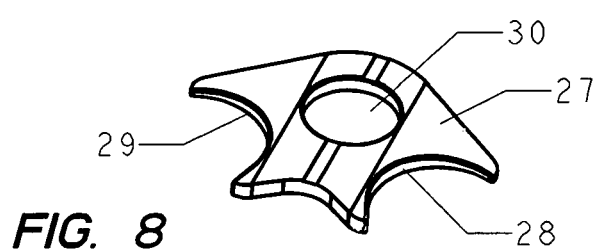
FIG. 8 is a perspective view of the cam cover plate.

As shown in FIGS. 3 and 4, the bone screw apertures 14 and 15 are connected by a V-shaped slot therebetween. Cam 17 is positioned at the midpoint of the "V". Wedge shoe 25 is slidably positioned between the cam 17 and bone screw aperture 14. Although a V-shaped slot is the preferred embodiment, any nonlineal shaped slot may be employed. A cam cover plate 27, as shown in FIG. 8, closes each slot and forms a portion of the distal surface 19 of the bone plate. The cam cover plate extends transversely along the distal surface of the bone plate between the apertures. Each end 28 and 29 of the cover plate has an arcuate shape conforming to the shape of the countersunk apertures.

Figure 6:
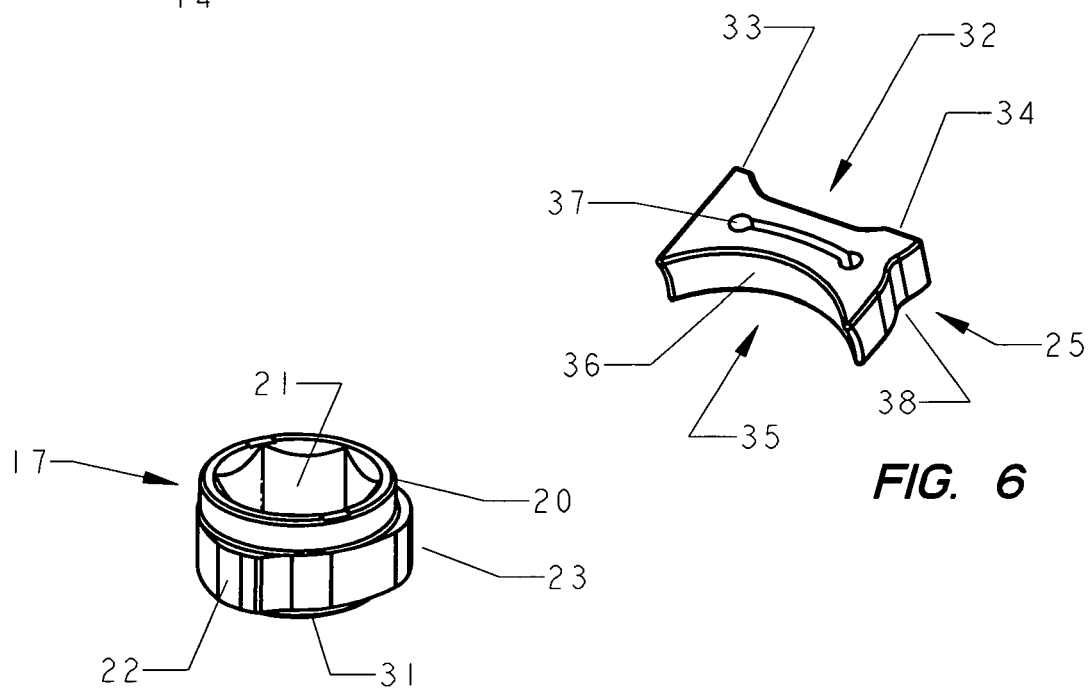
FIG. 6 is a perspective view of a wedge shoe.

As seen in FIG. 6 the wedge shoes 25 and 26 are formed with a surface 32 which conforms to the head 101 of the screw 100 or pin 200. They also include contact points 33 and 34 at the ends of the surface 32 and adjacent the sides of the shoes to insure more than a single positive pressure point of the shoe bearing against the head of the screw. This helps to prevent the screw from rotating and backing out once it has been installed. The opposite end of the shoes is provided with an indentation 36. This indentation acts in conjunction with the cam lobe surfaces 22 and 23 to prevent the cam lobe surfaces from rotating and releasing pressure against the wedge shoes thereby disengaging them from the head of the bone screws.

Wedge shoes 25 and 26 are also provided with a slot 37 which acts as a spring to maintain the shoe in contact with the head of the bone screw. When the cam is rotated such that the cam lobe surfaces 22 and 23 move the wedge shoes in contact with the head of the bone screws the width of the slot is decreased as it is placed under compression. This compressive force acts like a compressed spring to maintain the wedge shoe in contact with the head of the bone screw. Each wedge shoe 25 and 26 is also provided with a groove 38 which operates in conjunction with protrusion 40 on the side of each of the slots 42 and 44. As the wedge shoe is moved toward the bone screw by the cam surfaces 22 and 23, the protrusion moves from a forward portion to a rearward portion of the groove 38. This movement imparts a "snapping" action to the wedge shoe which is translated to the cam and the cam actuator. This "snapping" action acts as an tactile indicator to the surgeon or whomever is installing the device that the cam has been rotated sufficiently to move the wedge shoes into complete engagement with the bone screw heads. Since the elements of the bone screw plate are small and the distance that the wedge shoe travels is very small it is difficult for a surgeon to determine when the cam has been rotated sufficiently to move the wedge shoe in complete engagement with the head of the bone screw. This "snapping" action eliminates this problem by providing a tactile feedback to the surgeon indicating that the shoe has moved sufficiently to properly engage the head of the bone screw.

The heads of the bone screws have a spherical shape which matches the countersunk portions of the apertures. This allows for some flexibility in the placement of the bone plate and bone screws to compensate for anatomical considerations or to gain a better grip in the bone. After the bone screws or pins have been tightened, the cam is rotated by the actuator. The cam lobe surfaces 22 and 23 engage the wedge shoes and move then toward the apertures. When the wedge shoes are fully engaged with the heads of the bone screws, the surfaces 22 and 23 of the cam are disposed in indentations 36 of the wedge shoes and cannot freely move therefrom thereby locking the wedge shoe in engagement with the head of the bone screw.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A bone fastener locking system for a bone plate comprising:

a bone plate having at least two apertures each adapted for accepting a bone fastener, a substantially V-shaped channel extending between each of said at least two apertures, a rotatable cam positioned about an apex of said V-shaped channel, said cam being constructed and arranged to engage a free floating wedge shoe constrained by the inner surfaces in each leg of each of said V-shaped channel, said rotatable cam having a cam surface in contact with both of said wedge shoes, said cam rotatable to cause traversal of both of said wedge shoes along a respective leg of said V-shaped channel, said wedge shoes traversable between a disengaged position and an engaged position, whereby said disengaged position allows a bone fastener to be inserted into or removed from either of said respective at least two apertures and whereby said engaged position prevents substantial movement of a bone fastener placed in either of said respective at least two apertures.

2. The bone fastener locking system for a bone plate of claim 1 wherein each said wedge shoe engages a side surface of a respective said bone fastener.

3. The bone fastener locking system for a bone plate of claim 1 wherein said wedge shoes are enclosed within said bone plate.

4. A bone plate for attachment to bone across discontinuities comprising:

an elongated span having a first end and a second end, a first bracket on said first end and a second bracket on said second end, said first bracket having at least two apertures adapted to receive bone fasteners, a substantially V-shaped channel extending between said at least two apertures, a rotatable cam positioned about an apex of said V-shaped channel, said cam being constructed and arranged to engage a free floating wedge shoe constrained by the inner surfaces in each leg of said V-shaped channel and said rotatable cam, said rotatable cam having a cam surface in contact with said wedge shoes, said cam rotatable to cause traversal of each of said wedge shoes along a respective leg of said V-shaped channel between a disengaged position and an engaged position, whereby said disengaged position allows a bone fastener to be inserted into or removed from either of said at least two apertures and whereby said engaged position prevents substantial movement of a bone fastener placed in either of said at least two apertures.

5. The bone plate of claim 4 wherein said second bracket includes at least two apertures adapted to receive bone fasteners, a substantially V-shaped channel extending between said at least two apertures, a rotatable cam positioned at about an apex of said V-shaped channel, said cam being constructed and arranged to engage a free floating wedge shoe constrained by the inner surfaces in each leg of said V-shaped channel and said rotatable cam, said rotatable cam having a cam surface in contact with said wedge shoes, said cam rotatable to cause traversal of each said wedge shoe along a respective leg of said V-shaped channel between a disengaged position and an engaged position, whereby said disengaged position allows a bone fastener to be inserted into or removed from either of said at least two apertures and whereby said engaged position prevents substantial movement of a bone fastener placed in either of said at least two apertures.

6. A bone plate for attachment to bone across discontinuities comprising an elongated span having a first end and a second end, a first bracket on said first end and a second bracket on said second end, said first and said second bracket each having at least two apertures adapted to receive bone fasteners, said first bracket and said second bracket each having a substantially V-shaped channel therein extending between said at least two apertures, said channel including a plurality of internal surfaces, a rotatable cam positioned about an apex of said V-shaped channel, a free-floating wedge shoe disposed in each leg of said V-shaped channel, said rotatable cam having a cam surface in contact with each of said wedge shoes, each of said wedge shoes constrained by said plurality of internal channel surfaces and said cam surface, whereby rotation of said rotatable cam causes traversal of each of said wedge shoes along a respective leg of said V-shaped channel to prevent substantial bone fastener rotation.

7. The bone plate of claim 6 comprising a countersunk bore surrounding at least one of said at least two apertures, said countersunk bore having a sidewall, said wedge shoe extending through a portion of said sidewall during rotation of said rotatable cam.

8. The bone plate of claim 6 comprising a countersunk bore surrounding each of said at least two apertures, said bores each having sidewall, said wedge shoes extending through a portion of said sidewall during rotation of said rotatable cam.

9. The bone plate of claim 6 wherein at least one of said wedge shoes is provided with a spring means to maintain said wedge shoe in contact with a head of a bone screw positioned in said aperture after said rotatable cam moves said wedge shoe into said aperture.

10. The bone plate of claim 6 wherein each of said wedge shoes is provided with a spring means to maintain said shoes in contact with a head of a bone screw positioned in said aperture after said cam moves said shoes into said apertures.

11. The bone plate of claim 6 wherein at least one of said wedge shoes is provided with an indicator which indicate that said wedge shoe has been slid sufficiently into said aperture to engage a head of a bone screw positioned in said aperture.

12. The bone plate of claim 11 wherein the indicator comprises a groove on said at least one wedge shoe, said groove positioned on a surface of said at least one wedge shoe that is constrained by said rotatable cam.

13. The bone plate of claim 6 wherein each of said wedge shoes is provided with an indicator which indicate that said wedge shoes have been slid sufficiently into said apertures to engage a head of a bone screw positioned in said aperture.

14. The bone plate of claim 13 wherein the indicator comprises a groove on each of said at least two wedge shoes, said groove positioned on a surface of said at least one wedge shoe that is constrained by said rotatable cam.

15. The bone plate of claim 6 wherein at least one of said wedge shoes includes an end constructed and arranged to engage a bone fastener positioned in said aperture.

16. The bone plate of claim 15 wherein at least one of said wedge shoes includes an other end constructed and arranged to lock said rotatable cam in a position subsequent to a cam lobe surface engaging said wedge shoe.

17. The bone plate of claim 6 wherein each of said at least two wedge shoes an end constructed and arranged to engage a bone fastener positioned in said aperture.

18. The bone plate of claim 17 wherein each of said wedge shoes includes an other end constructed and arranged to lock said rotatable cam in a position subsequent to a cam lobe surface engaging said wedge shoes.

\* \* \* \* \*